United States Patent
Reinhard et al.

(10) Patent No.: US 10,560,691 B2
(45) Date of Patent: Feb. 11, 2020

(54) SYSTEM, HAVING A PROCESSING DEVICE AND A CAMERA CONNECTED THERETO, FOR THE DETECTION OF A MACHINE-READABLE SECURITY FEATURE OF A VALUE DOCUMENT AND METHOD FOR EXCHANGING A CAMERA OF SUCH A SYSTEM

(71) Applicant: CI Tech Sensors AG, Burgdorf (CH)

(72) Inventors: Christoph Reinhard, Burgdorf (CH); Mathias Zenger, Burgdorf (CH)

(73) Assignee: CI Tech Sensors, AG, Burgdorf (CH)

( * ) Notice: Subject to any disclaimer, the term of this patent is extended or adjusted under 35 U.S.C. 154(b) by 0 days.

(21) Appl. No.: 16/224,132

(22) Filed: Dec. 18, 2018

(65) Prior Publication Data
US 2019/0238829 A1 Aug. 1, 2019

(30) Foreign Application Priority Data
Dec. 22, 2017 (EP) .................................... 17210068

(51) Int. Cl.
*H04N 17/00* (2006.01)
*B42D 25/36* (2014.01)
(Continued)

(52) U.S. Cl.
CPC ........... *H04N 17/002* (2013.01); *B42D 25/36* (2014.10); *G01N 21/6456* (2013.01);
(Continued)

(58) Field of Classification Search
CPC .... H04N 17/002; H04N 5/247; H04N 5/2256; G07D 7/121; G07D 2207/00;
(Continued)

(56) References Cited

U.S. PATENT DOCUMENTS

2009/0132195 A1* 5/2009 Holl .................. G07D 7/00
702/104

FOREIGN PATENT DOCUMENTS

DE 102007038752 A1 2/2009
EP 1265464 A2 * 12/2002 ......... H01L 21/4867
(Continued)

OTHER PUBLICATIONS

Extended European Search Report filed in corresponding European Application; 6 pages.

*Primary Examiner* — Jefferey F Harold
*Assistant Examiner* — Human M Satti
(74) *Attorney, Agent, or Firm* — Black, McCuskey, Souers & Arbaugh, LPA

(57) ABSTRACT

A system including a processing device and an exchangeable camera connected thereto for detecting a machine-readable security feature of a valuable document. The system is calibrated by means of processing device correction data, which relate to characteristics of the processing device, and camera calibration data, which relate to the characteristics of the processing device and of the camera connected thereto. The camera includes a memory configured to store the processing device correction data and the camera calibration data relating to the System in which the calibration is carried out, and the processing device includes a memory configured to store the processing device correction data and the camera calibration data relating to the system in which operation for detecting a machine-readable security feature of the valuable document is carried out.

14 Claims, 5 Drawing Sheets

(51) Int. Cl.
*G01N 21/64* (2006.01)
*G07D 7/121* (2016.01)
*H04N 5/225* (2006.01)
*H04N 5/247* (2006.01)
*B42D 25/23* (2014.01)
*B42D 25/24* (2014.01)
*B42D 25/29* (2014.01)

(52) U.S. Cl.
CPC ............ *G07D 7/121* (2013.01); *H04N 5/2256* (2013.01); *H04N 5/247* (2013.01); *B42D 25/23* (2014.10); *B42D 25/24* (2014.10); *B42D 25/29* (2014.10); *G07D 2207/00* (2013.01)

(58) Field of Classification Search
CPC ........ B42D 25/36; B42D 25/29; B42D 25/24; B42D 25/23; G01N 21/6456
See application file for complete search history.

(56) References Cited

FOREIGN PATENT DOCUMENTS

| | | | |
|---|---|---|---|
| JP | H04881 A | | 1/1992 |
| JP | 2001174690 A | * | 6/2001 |

* cited by examiner

SYSTEM, HAVING A PROCESSING DEVICE AND A CAMERA CONNECTED THERETO, FOR THE DETECTION OF A MACHINE-READABLE SECURITY FEATURE OF A VALUE DOCUMENT AND METHOD FOR EXCHANGING A CAMERA OF SUCH A SYSTEM

CROSS-REFERENCE TO RELATED APPLICATION

This application claims priority to and claims the benefit of European Patent Application Serial No. 17 210 068.7, which was filed Dec. 22, 2017.

TECHNICAL FIELD

The invention relates to a system, comprising a processing device and a camera connected thereto, for detecting a machine-readable security feature of a valuable document, and a method for exchanging a camera of such a system.

BACKGROUND

Valuable documents such as security papers or e.g. banknotes, cheques, shares, papers having a security imprint, certificates, identity cards, passports, entrance tickets, travel tickets, vouchers, identification or access cards or the like can be provided with security features on their front side, their rear side and/or in a manner embedded in the material, in order to hamper or to prevent forgery thereof and to be able to check the authenticity thereof. In the exemplary case of a banknote, some of said security features, e.g. a region of the banknote that is printed with luminescent ink, may be machine-testable.

Conventional apparatuses for handling such banknotes which are installed e.g. in automated teller machines for issuing banknotes are equipped inter alia with systems that check the authenticity of the banknotes on the basis of the machine-readable security features in order to remove them from circulation, if appropriate, if a banknote is identified as counterfeit. In this case, the security features are detected by sensors, and the signals are processed and evaluated by a processing device of the system. In order to ensure reliable detection of the security features, the system has to be calibrated e.g. with regard to the security features to be checked. Since both the sensors, e.g. cameras, and components of the processing device, e.g. analogue-to-digital converters for the cameras, have tolerances, a joint calibration of the sensors with the processing device leads to a dependence of the calibration on characteristics of the sensors and of the processing device, that is to say that they are coordinated with one another by the calibration. For the case where one sensor is intended to be exchanged for another after calibration, e.g. on account of a failure of the sensor, in conventional systems the entire system has to be exchanged since a renewed calibration cannot be carried out with systems that have already been installed in an automated teller machine.

Consequently, in conventional systems there is a problem to the effect that in the event of a failure of a component of the system, the entire system has to be exchanged.

SUMMARY

In response to this, a system comprising a processing device and an exchangeable camera connected thereto, and also a method for exchanging a camera of such a system are provided.

The system in accordance with one embodiment can comprise a processing device and at least one camera (e.g. two, three, four, five, six, etc.) connected thereto. The system can be part of an apparatus for handling valuable documents, which can be configured for receiving valuable documents, for transporting the valuable documents through the apparatus by means of a transport apparatus, and for testing and outputting the valuable documents. The valuable document (e.g. a banknote) can be a flat, e.g. rectangular, article composed of e.g. paper or other fibrous material, plastic or a combination thereof and can have at least one machine-readable security feature. The system can be provided e.g. in an automated teller machine. Moreover, the system can likewise be provided in numerous types of automatic machines which handle valuable documents, e.g. in automatic payment machines, automatic ticket machines, and food and drinks vending machines. The construction and the function of such automatic machines are sufficiently known, and so they will not be described. The processing device can be provided e.g. as a populated circuit board (e.g. a printed circuit board) having fitted thereon (e.g. integrated) circuits, e.g. microprocessors (e.g. a central processing unit; hereinafter for short: CPU), memory modules, analogue-to-digital converters (hereinafter for short: A/D converters), interfaces for connecting the cameras and for communication with other components of the handling apparatus, etc. By way of example, the processing device can comprise at least one CPU, one memory, one A/D converter and one interface, wherein the CPU can perform the function of a control unit of the processing device. The individual components of the system can be connected to one another by corresponding (e.g. electrical and/or optical) lines for communication and/or power supply.

The camera can be connected to the processing device and can detect a security feature of the valuable document, e.g. if the valuable document is transported past the camera. The camera is e.g. configured to be exchangeable. Furthermore, instead of a camera, it is also possible to use e.g. a sensor that uses a different detection principle, e.g. a magnetic, capacitive, inductive, or tactile sensor.

The system can be calibrated by means of processing device correction data, which relate to characteristics of the processing device, and camera calibration data, which relate to characteristics of the processing device and of the camera connected thereto. The calibration can serve e.g. to adjust the system to the security features to be detected. The characteristics can relate e.g. to differences between expected output values when detecting a standard (e.g. standard values) and actual output values, e.g. on account of tolerances of the system, when detecting the standard. A standard can be e.g. an ideally white body (white reference body) that is detected by the camera in order to compare the output voltage thereof when detecting the standard with a predetermined output voltage (e.g. in accordance with a manufacturer's specification when detecting the standard) and to determine the differences that occur. Such differences in the output values of the camera can occur e.g. on account of different detection sensitivities. Analogously thereto, differences can also occur during the processing of the output voltage of the camera in the processing device e.g. on account of tolerances of the A/D converters. The processing device correction data and the camera calibration data can be present e.g. as binary and machine-readable and can comprise parameters (e.g. state information of the camera and/or of the processing device such as hardware and/or software version information), values (e.g. normalization values such as weighting values, calibration values, etc. and boundary conditions such as e.g. reference voltages, etc.), settings of the processing device and/or of the camera (e.g. a transport speed of the valuable document, a camera distance with respect to the valuable document, etc.) and instructions, method steps, etc.

The camera can comprise e.g. a memory (e.g. one memory module or a plurality of memory modules) configured e.g. to store the processing device correction data and the camera calibration data relating to the system in which the calibration is carried out. By way of example, the calibration can be carried out using a calibration device to which the cameras are connected and which comprises an e.g. ideal (exhibiting low tolerances) or simulated processing device. Consequently, cameras of a plurality of systems can be calibratable by such a calibration device, e.g. after the production of the cameras. The memory can be configured e.g. to store the processing device correction data and the camera calibration data permanently, e.g. until they are changed by the calibration device. The memory can be e.g. externally addressable e.g. by the CPU of the connected processing device. Hereinafter, a camera which holds in its memory its camera calibration data and the processing device correction data of the processing device by means of which the calibration is carried out is referred to as a calibrated camera.

The camera can furthermore comprise e.g. an image sensor (e.g. a linear-array sensor, a contact image sensor, etc.) and an illumination means coordinated with the sensitive wavelength of the image sensor or with the spectrum of the security feature to be detected, e.g. one or a plurality of light-emitting diode(s) (hereinafter for short: LED; e.g. one or a plurality of organic LED(s)). The illumination means can illuminate the valuable document in order to activate optical properties of the security feature, e.g. a fluorescence, a reflection, etc., which is detectable by the image sensor of the camera. The image sensor can comprise a plurality of detector elements, for example, which output separate signals for corresponding pixels. Furthermore, the camera can comprise a plurality of image sensors, e.g. in order to be able to detect colours or security features in different spectral ranges.

The camera can be embodied e.g. as a camera pair comprising a first and a second camera. The first camera can be configured e.g. to detect reflected light that is emitted by the LED and is reflected by the valuable document, and the second camera can be configured e.g. to detect transmitted light that is emitted by the LED and passes through the valuable document. Consequently, e.g. security features present within the valuable document are detectable.

The processing device can comprise e.g. a memory (e.g. one memory module or a plurality of memory modules), configured e.g. to store the processing device correction data and the camera calibration data relating to the system in which operation for detecting a machine-readable security feature of the valuable document is carried out. The processing device correction data can be obtained e.g. by connecting the processing device to a normalization device, which simulates e.g. an ideal (exhibiting low tolerances) camera and outputs simulated camera signals to the processing device, wherein the processing device creates and stores the processing device correction data on the basis of the (ideal) simulated camera signals. The memory can be configured e.g. to store the processing device correction data permanently and the camera calibration data permanently or non-permanently. The memory can be addressable e.g. by the CPU of the processing device. Hereinafter, a processing device that holds its processing device correction data in its memory is referred to as a normalized processing device.

The processing device (e.g. the CPU) can furthermore be configured to calculate the camera calibration data—to be stored in the memory of the processing device—of the system in which operation for detecting the machine-readable security feature of the valuable document is carried out. The camera calibration data can be calculated e.g. upon each start of the system. The calculation can be carried out by weighting the camera calibration data stored in the memory of the camera with the processing device correction data stored in the memory of the camera and with the processing device correction data stored in the memory of the processing device. Consequently, the camera calibration data used in the system are adaptable on the basis of the processing device correction data. This has the consequence that the camera calibration data are adaptable to the current system, that is to say that cameras which are calibrated in different systems are mutually interchangeable.

The camera calibration data can comprise e.g. at least one of the following items of information which are determinable in the context of the calibration of the camera: a white reference value of the camera (e.g. a neutral white value without a colour component, e.g. a corresponding output voltage of the camera when detecting a white reference), a camera illumination value (e.g. a value of a current flow through the LED), a camera colour value (e.g. a colour value for red, green and/or blue, e.g. a corresponding output voltage of the camera when detecting a red, green and blue colour), a resolution of the camera, a distance value of the camera with respect to the valuable document, and a transport speed value of the valuable document relative to the camera.

By way of example, the white reference value, the camera illumination value and the camera colour value are determined for predetermined distances and transport speeds. The camera calibration data can be determined separately e.g. for each pixel of the camera or for pixels combined in channels. The processing device correction data can relate e.g. to output values which are determinable by the processing device in response to the input of one of the following voltages in the context of the normalization of the processing device: a camera reference voltage, e.g. as reference value for comparison with camera output voltages, a camera bright level voltage, which represents e.g. a maximum brightness value of the camera if a bright, e.g. white, region of a valuable document is detected, a camera dark level voltage, which represents e.g. a maximum dark value of the camera if a dark, e.g. black, region of a valuable document is detected, a camera bright level mean value voltage, which is averaged e.g. from a plurality of camera bright level voltages over a predetermined period of time, a camera dark level mean value voltage, which is averaged e.g. from a plurality of camera dark level voltages over a predetermined period of time, and an amplification voltage, e.g. with which the output voltages of the camera are amplified by amplifiers of the processing device. The processing device correction data can be determined separately e.g. for each pixel of the camera or for pixels combined in channels.

The memory of the camera can be a non-volatile memory, e.g. an EEPROM (Electrically Erasable Programmable Read Only Memory). Furthermore, other types of non-volatile memories can be used, e.g. other semiconductor memories or magnetic memories or optical memories. Furthermore, the memory of the processing device in which the processing device correction data are stored can be a non-volatile memory in the manner of the memory of the camera.

Furthermore, the memory of the processing device in which the camera calibration data are stored can be a volatile memory, e.g. a RAM. Furthermore, other types of volatile memories can be used, e.g. other semiconductor memories or magnetic memories.

The valuable document can be e.g. one of the following: a banknote, a cheque, an identity card, a passport, a ticket and a share document.

The method for exchanging a camera in a system comprising a processing device and an exchangeable camera connected thereto for detecting a machine-readable security feature of a valuable document in accordance with one exemplary embodiment can comprise: exchanging a first camera, which is connected to a first processing device, for a second camera, which is calibrated by means of a second processing device and which has second camera calibration data and second processing device correction data in a memory, reading out, by means of the first processing device (e.g. the CPU), the second camera calibration data and the second processing device correction data from the memory of the second camera, calculating, by means of the first processing device, adapted camera calibration data for the system comprising first processing device and second camera by weighting the second camera calibration data with the second processing device correction data and with first processing device correction data stored in a memory of the first processing device, and applying, by means of the first processing device (e.g. the CPU), the adapted camera calibration data by means of storage in the (e.g. volatile) memory of the first processing device. These steps can e.g. be stored as software in the memory of the processing device or a further storage medium of the processing device and be implementable by the CPU.

The processing device correction data can be obtained e.g. by the following method (e.g. after production and before incorporation of the system into an apparatus for handling valuable documents or during the repair of such an apparatus): connecting a normalization device, which simulates e.g. a calibrated camera, to the processing device, outputting, by means of the normalization device, a simulated (e.g. ideal, i.e. exhibiting little interference) camera signal, and determining, by means of the processing device, the processing device correction data on the basis of the simulated camera signal.

The processing device can be normalized e.g. using the normalization device by storing the determined processing device correction data in the (e.g. non-volatile) memory of the processing device.

The camera calibration data can be obtained e.g. by the following method (e.g. after production and before incorporation of the system into an apparatus for handling valuable documents): connecting a camera to be calibrated to the normalized processing device, detecting, by means of the camera, a calibration standard (e.g. a white reference standard, a red-coloured, green-coloured and blue-coloured reference standard, etc.) and outputting a corresponding camera signal (e.g. a voltage signal) to the processing device, and determining, e.g. by means of the processing device or e.g. a calibration device connected thereto, the camera calibration data on the basis of the camera signal that is output to the processing device in response to the calibration standard. By way of example, the method can be carried out in a manner controlled by the calibration device connected to the processing device (e.g. by means of one of the interfaces).

The camera can be calibrated e.g. using the normalized processing device by storing the determined camera calibration data together with processing device correction data of the processing device in the (e.g. non-volatile) memory of the camera.

BRIEF DESCRIPTION OF THE DRAWINGS

Exemplary embodiments of the apparatus and of the method are illustrated in the figures and are explained in greater detail below.

FIG. 2 shows signals of a camera and of a processing device, wherein

DETAILED DESCRIPTION

In the following detailed description, reference is made to the accompanying drawings, which form part of this description and show for illustration purposes specific embodiments in which the invention can be implemented. It goes without saying that the indexing of features with e.g. "first", "second", etc. serves only for illustration and is not restrictive in any way whatsoever. It goes without saying that the features of the various exemplary embodiments described herein can be combined with one another, unless specifically indicated otherwise. Therefore, the following detailed description should not be interpreted in a restrictive sense, and the scope of protection of the present invention is defined by the appended claims. In the figures, identical or similar elements are provided with identical reference signs, in so far as this is expedient.

In the context of this description, the terms "connected" and "coupled" are used to describe both a direct and an indirect connection, and a direct or indirect coupling.

By way of example, the herein described circuits or parts thereof or the microprocessors, e.g. the CPU and/or the A/D converter, can be implemented using at least one of the following components: an application specific integrated circuit (ASIC), a digital signal processor (DSP), a digital signal processing device (DSPD), a programmable logic device (PLD) and a field programmable gate array (FPGA). The memory used can be for example an electrically erasable and programmable read-only memory (EEPROM) and a random access memory (RAM), wherein other volatile and non-volatile memories are also possible. Furthermore, method steps can be carried out e.g. in a manner implemented by hardware and/or software, i.e. can be present as instructions in the form of a software code, e.g. in the memory of the processing device and/or in a memory of the apparatus for handling valuable documents, and can be executed by e.g. the microprocessors.

The term "camera" used herein includes optical detection apparatuses which detect an image and convert it into electrical signals, independently of the construction thereof and the physical principle of action thereof, i.e. optoelectronic image converters that operate with different radiation spectra. Usable spectra can be e.g.: a visible spectrum, e.g. in a range of approximately 380 nm-750 nm, an infrared spectrum, e.g. in a range of approximately 750 nm-3000 nm, and an ultraviolet spectrum, e.g. in a range of approximately 1 nm-380 nm.

Figure 1:
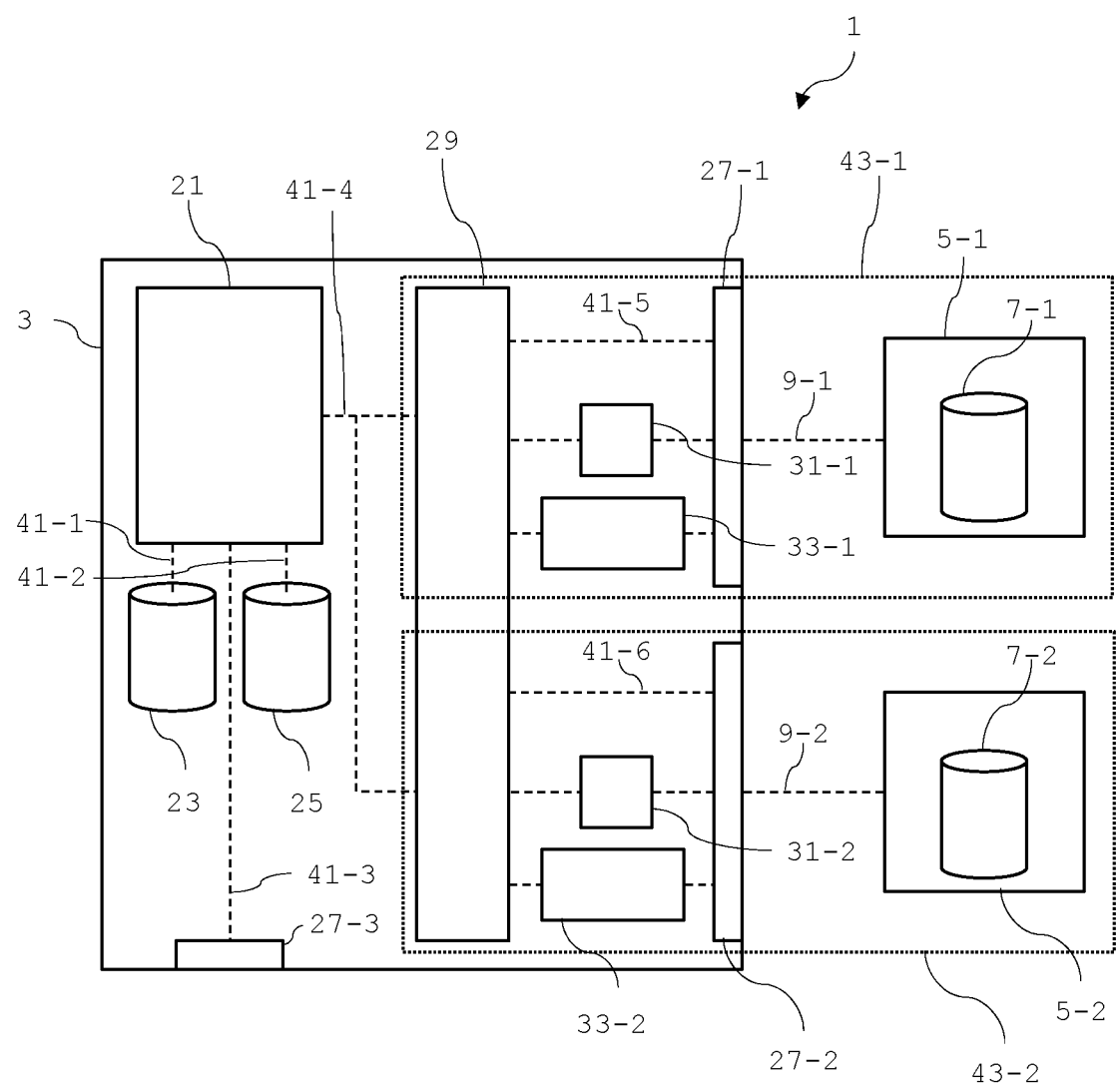
FIG. 1 shows a schematic construction of a system comprising a processing device and two cameras.

FIG. 1 schematically shows a system 1 comprising a processing device 3 with a first and a second camera 5-1, 5-2 connected thereto. The system is installed e.g. in a handling apparatus for banknotes (not shown), which is in turn installed e.g. in an automated teller machine (not shown). The cameras 5-1, 5-2 are configured to detect banknotes that are transported past them and to output corresponding signals to the processing device 3. By way of example, the first camera 5-1 is configured as a reflected-light camera, which detects light reflected at the banknote. The second camera is configured as a transmitted-light camera, which detects light passing through the banknote. The two cameras 5-1, 5-2 are sensitive in the visible spectrum, wherein the second camera 5-2 can additionally be sensitive in the (e.g. near-) infrared spectrum. By way of example, the second camera 5-2 can be sensitive to two different wavelengths in the infrared spectrum. The processing device 3 ascertains on the basis of the signals, e.g. by comparing them with stored detection signals of different security features, whether or not a security feature of the banknote was detected.

The cameras 5-1, 5-2 each comprise at least one LED (not shown) for irradiating (illuminating) the banknote and an image sensor (not shown) for detecting a security feature of the banknote, wherein the LED(s) is (are) coordinated with the spectrum of the image sensor. The image sensor can be embodied e.g. as a linear-array sensor for the visible optical spectrum having a fixed number of detector elements corresponding to individual pixels of the banknote to be detected. The individual detector elements can be combined in channels. Furthermore, the first camera 5-1 comprises a first EEPROM 7-1 as memory and the second camera 5-2 comprises a second EEPROM 7-2 as memory and the first camera 5-1 is connected to the processing device 3 by means of a first line 9-1 and the second camera 5-2 is connected to the processing device 3 by means of a second line 9-2. The lines 9-1, 9-2 serve for signal transmission between the processing device 3 and the cameras 5-1, 5-2 and can furthermore supply the cameras 5-1, 5-2 with electrical energy.

The processing device 3 comprises a CPU 21, a RAM 23 and an EEPROM 25 as memory, a first, a second and a third interface 27-1, 27-2, 27-3, an FPGA 29, a first and a second LED driver 31-1, 31-2 and also a first and a second digital converter 33-1, 33-2. The RAM 23 and the CPU 21 are connected to one another by a first line 41-1, the EEPROM 25 and the CPU 21 are connected to one another by a second line 41-2, and the third interface 27-1 and the CPU 21 are connected to one another by a third line 41-3. The CPU 21 is furthermore connected to the FPGA 29 by a fourth line 41-4. Furthermore, the FPGA 29 is connected to the first and second interfaces 27-1, 27-2 by means of a fifth and a sixth line 41-5, 41-6, respectively. Likewise, the LED drivers 31-1, 31-2 and the digital converters 33-1, 33-2 are connected both to the FPGA 29 and to the associated one of the interfaces 27-1, 27-2 by means of respective lines. For the case where the cameras 5-1, 5-2 comprise a plurality of output channels, further digital converters and/or LED drivers can be provided in an analogous manner. Furthermore, the processing device 3 is provided with an energy supply apparatus (not shown), which supplies the components fitted thereon or connected thereto with electrical energy.

The CPU 21 is the control unit of the processing device 3, which can communicate with the other components via the lines 41-1 to 41-6, i.e. can output control commands and receive information. The CPU 21 executes a program (e.g. software) for detecting security features of banknotes, for which purpose it receives from the FPGA 29 image data (image data signals) based on the camera signals (detection signals) of the cameras 5-1, 5-2. By way of example, the CPU 21 is connected to other components by means of the interface 27-3, e.g. is connected to a communication system (e.g. a BUS system), and can exchange data e.g. with a central control unit of the handling apparatus and/or of the automated teller machine, e.g. communicate the fact that a banknote is a counterfeit if no security feature is detected.

A description is given below, for the first camera 5-1, of a signal transmission and signal processing path 43-1 proceeding from the camera 5-1 through to the CPU 21, wherein said path analogously also applies to the second camera 5-2 (signal transmission and signal processing path 43-2). In a manner controlled by the CPU 21 or the FPGA 29, the first LED driver 31-1 generates an illumination signal for the LED of the first camera 5-1, such that the LED irradiates the banknote and the camera 5-1 can detect a security feature, e.g. on the basis of a luminescence or a reflection. The first camera 5-1 detects the banknote by means of the image sensor during transport past the camera 5-1 and outputs a corresponding analogue detection signal (e.g. a voltage signal), e.g. for the colours red, green and blue and for a brightness, to the first interface 27-1, which signal is then forwarded to the first digital converter 33-1. The first digital converter 33-1 comprises e.g. an amplifier for each channel of the camera, a multiplexer and an A/D converter. The digital converter 33-1 converts the analogue detection signal of the camera 5-1 into a digital detection signal. The digital detection signal is processed further, e.g. filtered, and conditioned to form an image data signal by the FPGA 29. Said image data signal is forwarded to the CPU 21 for evaluation. The signal transmission and signal processing paths 43-1, 43-2 described above are of exemplary type and can be embodied using other components: by way of example, the FPGA 29 and the digital converters 33-1, 33-2 and also the LED drivers 31-1, 31-2 can be integrated in a circuit, the cameras 5-1, 5-2 can comprise a plurality of image sensors and, consequently, further digital converter can be necessary or further components such as e.g. additional signal filters can be present.

What the signal transmission and signal processing paths have in common is that, on account of different tolerances of the (e.g. structurally identical) component parts used therein, the signals can be processed differently in the signal transmission and signal processing paths; by way of example, on account of image sensors having different degrees of sensitivity (e.g. noise) when detecting an optically identical reference under identical conditions, two structurally identical cameras may output analogue detection signals that deviate from one another, and e.g. the amplifiers of the digital converters may amplify the analogue detection signals differently, such that mutually different digital detection signals are generated proceeding from the optical reference. Furthermore, since the signal transmission and signal processing paths have components of the processing device and of the camera, signals transmitted via said paths are subjected to the characteristics of both the processing device and the camera. However, since reliably detecting a security feature of a banknote necessitates setting the system to e.g. the type of expected security features, the transport speed of the banknote, the type of camera arrangement (e.g. transmitted light/reflected light, in pairs), etc., the above-described tolerances in the signal transmission and signal processing paths have to be compensated for. In the case of the combination of a transmitted-light camera with a reflected-light camera, for example, these two cameras have to be adjusted to one another. The tolerances are taken into account by the calibration of the cameras and by the normalization of the processing device, wherein corresponding processing device correction data and camera calibration data are generated, on the basis of which the detection signals are corrected. Consequently, the processing device correction data and the camera calibration data are dependent on characteristics of the processing device and of the camera.

The processing device correction data and camera calibration data are (have been) stored in the first and second EEPROMs 7-1, 7-2 of the cameras 5-1, 5-2, and the processing device correction data are (have been) stored in the EEPROM 25 of the processing device 3. Using the processing device correction data and the camera calibration data, it is possible for the CPU 21 to calculate adapted camera calibration data in order to use different cameras with different processing devices, i.e. it is possible to exchange a camera for an (e.g. structurally identical) camera without new calibration/normalization.

Characteristics of the camera and of the processing device and the influence thereof on the normalization (correction) of the processing device and the calibration of the camera are described with reference to FIG. 2. FIG. 2 shows signals of a camera and of a processing device, wherein FIG. 2A shows a camera signal and FIG. 2B shows a digital converter signal.

Figure 2A:
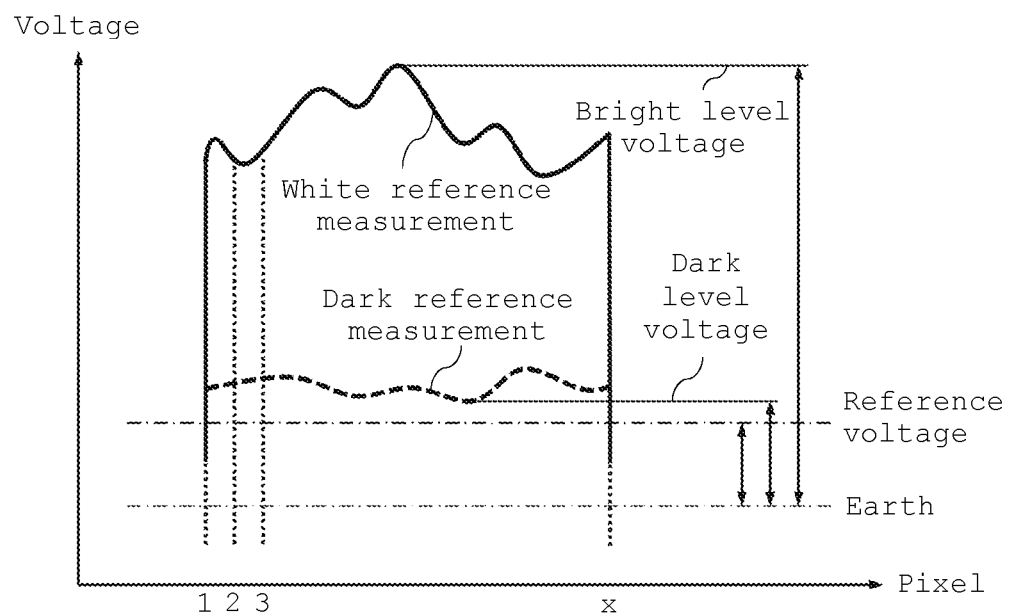
FIG. 2A shows a camera signal and FIG. 2B shows a digital converter signal.

FIG. 2A shows a camera signal, i.e. an analogue detection signal, which is output by the camera when carrying out a bright measurement and a dark measurement. The individual detector elements (pixels) each output a voltage signal depending on the detected standard, which voltage signals can be different on account of different sensitivity of the pixels. By way of example, the bright level voltage of the camera corresponds to the voltage signal of an ideal pixel when detecting a white reference (e.g. of a white reference body) and the dark level voltage of the camera corresponds to the voltage signal of an (e.g. different) ideal pixel when detecting a dark reference (e.g. of a dark reference body).

The differences between the individual pixels are represented in the camera calibration data of the camera in order to adapt the voltage signals of the individual pixels or of the channels to one another. By way of example, the output voltages of the pixels which do not attain the ideal bright level voltage are adapted with a calibration factor depending on the ratio to the bright level voltage. For a detected white reference body, the same voltage signals can thus be obtained for all pixels/channels. The camera calibration data can indicate e.g. a white reference and dark reference value of a pixel relative to an illumination value (e.g. by means of the LED) and a colour value (e.g. for red, green and blue). Furthermore, boundary conditions such as a distance value of the camera with respect to the valuable document and a transport speed value of the valuable document relative to the camera can also be taken into account in the camera calibration data. The individual pixels/channels of the camera are adaptable to one another in this way.

Figure 2B:
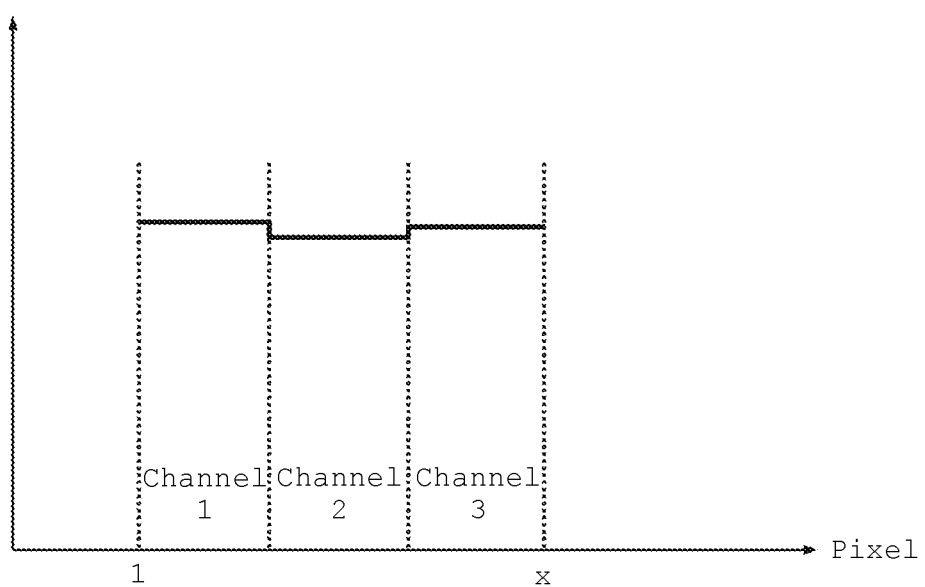

FIG. 2B shows an amplification signal of a digital converter of the processing device for, by way of example, three channels of a camera. That is to say that for example the pixels 1 to 100 are processed, i.e. amplified and converted into a digital detection signal, in one channel of the digital converter. It is evident that the channels, i.e. the grouping of individual pixels, are amplified differently in the digital converter. Consequently, the image information output for a pixel is dependent on the characteristics both of the pixel and of the digital converter. The processing device correction data can represent correction factors (normalization factors) which take account of the different processing of the analogue detection signals into digital detection signals in the channels of the digital converter; the analogue detection signals can be e.g. the following voltages: a camera reference voltage serving e.g. as reference for bright/dark/colour determination, a camera bright level voltage, which represents e.g. a maximum brightness value of the camera, a camera dark level voltage, which represents e.g. a maximum dark value of the camera, a camera bright level mean value voltage, which represents e.g. a voltage averaged over time and/or over all pixels of the image sensor, a camera dark level mean value voltage, which represents e.g. a voltage averaged over time and/or over all pixels of the image sensor, and an amplification voltage, which represents e.g. the signal amplification by the amplifier of the digital converter. The digital converters of the processing device and the camera are adaptable to one another in this way.

Figure 3:
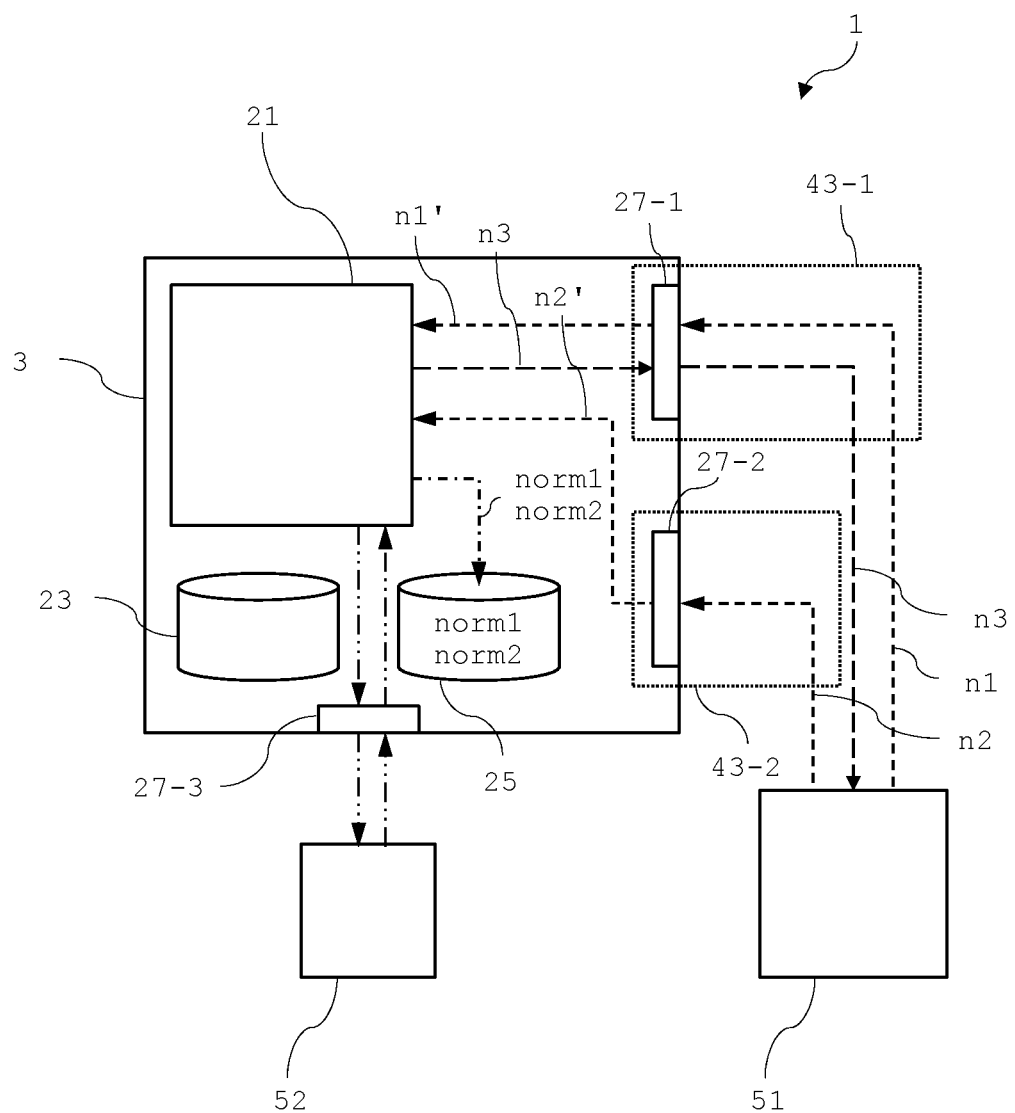
FIG. 3 shows a schematic for generating the processing device correction data in the course of normalizing (correcting) the processing device.
Figure 4:
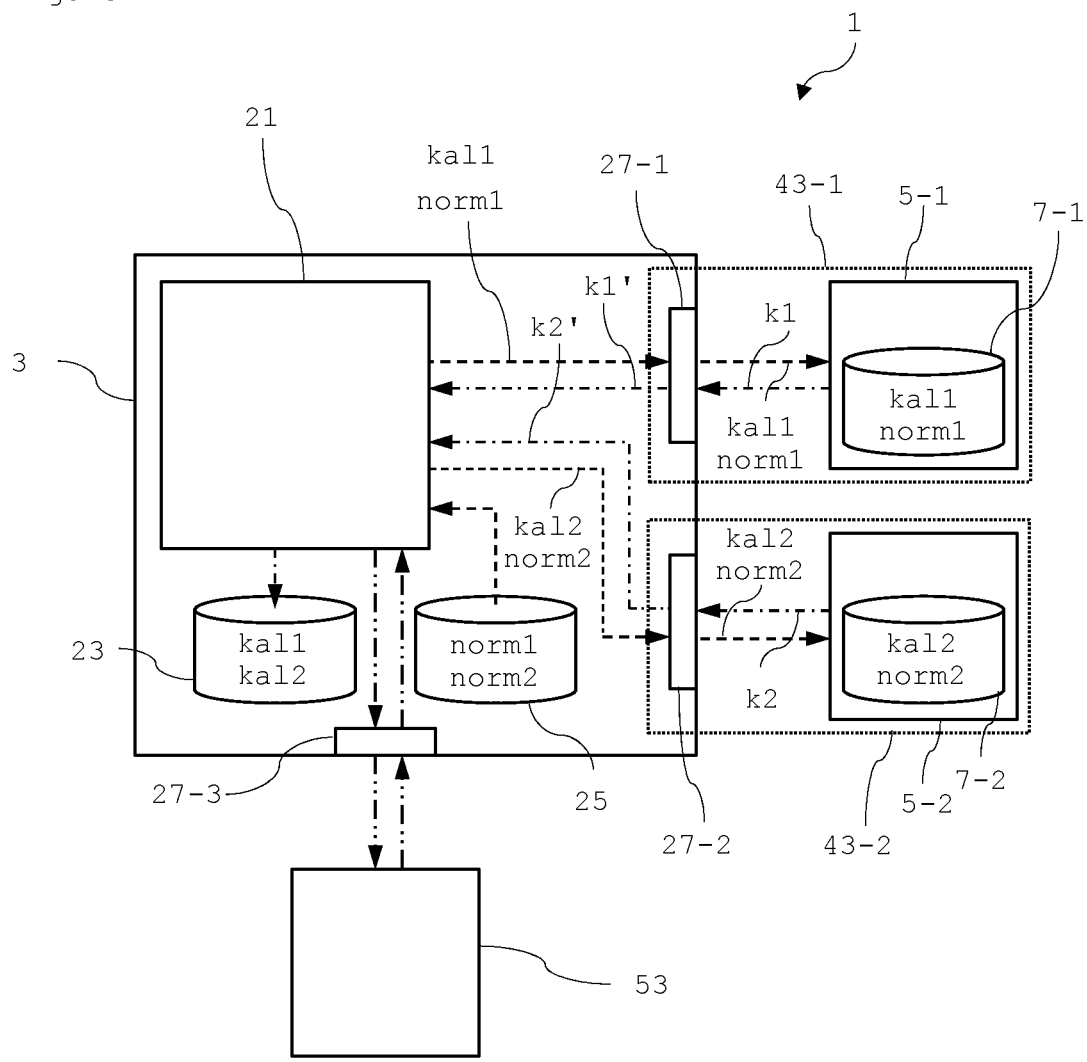
FIG. 4 shows a schematic for generating the camera calibration data and for using the processing device correction data and in the case of calibrating the camera.
Figure 5:
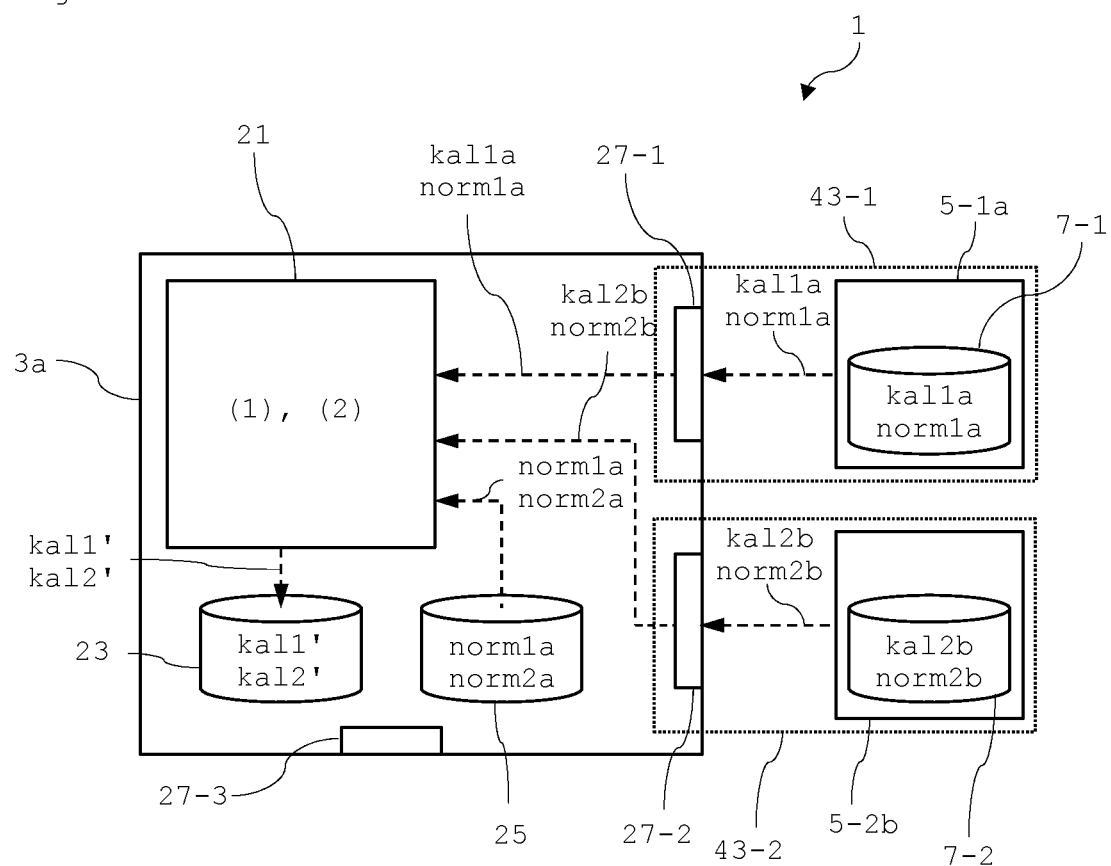
FIG. 5 shows a schematic for calculating adapted camera calibration data when exchanging a camera.

Processes and methods of generating the processing device correction data, the camera calibration data, the adapted camera calibration data and camera exchange are described below with reference to FIG. 3 to FIG. 5. In FIG. 3 to FIG. 5, the lines 41-1 to 41-6 and 9-1 and 9-2 and the components FPGA 29, LED drivers 31-1, 31-2 and digital converter 33-1, 33-2 of the signal transmission and signal processing paths 43-1, 43-2 are not shown, in order to enable better illustration; signal transmission processes are shown instead.

FIG. 3 shows a schematic for generating the processing device correction data when normalizing (correcting) the processing device.

For normalizing the processing device 3, a normalization device 51, which simulates a calibrated camera, is connected to the processing device 3 by means of the interfaces 27-1 and 27-2. Furthermore, a control device 52, which initiates the normalization process and serves as a user interface, is connected to the processing device 3 by means of the interface 27-3. Alternatively, the normalization device 51 and the control device 52 can be embodied as a single device that combines the functions described below with one another. As a further alternative, the control device 52 can be omitted if the processing device 3 itself has the functionality of the control device 52 as described below.

The control device 52 is provided and configured to give the user (the person who carries out the normalization) the opportunity to start, to monitor and to end the normalization process (e.g. to initiate individual steps thereof and to track the progress of the normalization process). For this purpose, the CPU 21 and the control device 52 communicate with one another by means of the interface 27-3. The control device 52 can be e.g. a customary PC, e.g. a laptop.

The normalization device 51 can be e.g. a test device in series production of the processing device 3 or a mobile device that is transportable e.g. to an automated teller machine for repair. The normalization device 51 outputs to the first and second interfaces 27-1, 27-2 respectively a first and a second simulated camera signal n1, n2 (e.g. a voltage signal), which correspond to the analogue detection signals of the cameras 5-1, 5-2. These simulated camera signals n1, n2 can be identical for both interfaces 27-1, 27-2 and serve as a standard for the processing device 3; by way of example, they are particularly low-noise and stable. The simulated camera signal n1, n2 is output for a predetermined time duration and with predetermined values; the bright level voltage, dark level voltage and reference voltage as shown in FIG. 2A are output by way of example. The transmission and processing in the respective signal transmission and signal processing path 43-1, 43-2 give rise to a first and second (e.g. digital) image data signal n1', n2' deviating from the first and second simulated camera signals n1, n2, said image data signals being transmitted to the CPU 21. The outputting of the simulated camera signals n1, n2 is controlled by the CPU 21, which, by means of a control signal n3, outputs corresponding commands to the normalization device 51 in order to initiate e.g. predetermined levels, sequences, etc. of the simulated camera signals n1, n2. The normalization device 51 can likewise be supplied with energy by the processing device 3. In the example in FIG. 3, one normalization device 51 is shown, which communicates with both interfaces 27-1 and 27-2, but a separate normalization device 51 can be used for each of the interfaces 27-1 and 27-2. Likewise, the control signal n3 can be output via each of the interfaces 27-1 and 27-2.

In response to the simulated camera signals n1, n2, the CPU 21 calculates the processing device correction data for the processing device 3, which comprise e.g. information about differences, which are determinable from the image data signal, of the individual pixels during the white reference and dark reference measurement. The processing device correction data are calculated separately for both signal transmission and signal processing paths 43-1, 43-2, that is to say that first processing device correction data norm1 are calculated for the first signal transmission and signal processing path 43-1 and second processing device correction data norm2 are calculated for the second signal transmission and signal processing path 43-2. Afterwards, the processing device correction data norm1, norm2 are stored in the EEPROM 25 by the CPU 21. In the processing device correction data norm1, norm2, the differences (characteristics of the processing device 3) during the processing of the simulated camera signals n1, n2 are taken into account and are used during operation of the system 1 for correcting the signals of the cameras 5-1, 5-2.

The processing device 3 is normalized by storing the processing device correction data norm1, norm2 in the EEPROM 25.

FIG. 4 shows a schematic for generating the camera calibration data and for using the processing device correction data when calibrating a camera.

For calibrating the cameras 5-1, 5-2, the latter are connected to the first and second interfaces 27-1, 27-2, respectively, of a normalized processing device 3. Afterwards, the cameras 5-1, 5-2, e.g. in successive calibration steps, detect a calibration standard, e.g. for bright, dark and colour values, and output a first and second analogue detection signal k1, k2 (e.g. a voltage signal) to the interfaces 27-1, 27-2. Detecting the calibration standard can be carried out under the control of a calibration device 53, for example, which is connected to the third interface 27-3 for this purpose, that is to say that the calibration device 53 can communicate with the CPU 21 in order to control the sequence of the individual calibration steps. The transmission and processing in the respective signal transmission and signal processing path 43-1, 43-2 gives rise to a first and second (e.g. digital) image data signal k1', k2' deviating from the analogue detection signal k1, k2, said image data signals being transmitted to the CPU 21. In addition, the calibration device 53 can transmit information regarding a distance between the camera and the banknote, a transport speed of the banknote, an image resolution of the camera, etc. to the CPU 21. From the image data signals k1', k2' and, if appropriate, the additional items of information transmitted by the calibration device 53, the CPU 21 calculates for the two signal transmission and signal processing paths 43-1, 43-2 respective first and second camera calibration data kal1, kal2 and transmits the latter together with its own processing device correction data norm1, norm2 to the cameras 5-1, 5-2 for storage in the EEPROMs 7-1, 7-2 thereof. Alternatively, the camera calibration data kal1, kal2 can be calculated by the calibration device 53 and transmitted to the CPU 21. By way of example, the first and second camera calibration data kal1, kal2 can also be stored in the RAM 23 of the processing device 3 or some other memory system (not shown) of the processing device 3. That is to say that the processing device correction data are calculated separately for both signal transmission and signal processing paths 43-1, 43-2, that is to say that first camera calibration data kal1 are calculated for the first signal transmission and signal processing path 43-1 and second camera calibration data kal2 are calculated for the second signal transmission and signal processing path 43-2. In the camera calibration data kal1, kal2, the differences (characteristics of the processing device 3, cf. the exemplary digital converter signal in FIG. 2B, and of the respective camera 5-1, 5-2, cf. the exemplary detection signal in FIG. 2A) are taken into account during the processing of the detection signals k1, k2 and are used during operation of the system 1 for correcting the detection signals of the cameras 5-1, 5-2. The cameras 5-1, 5-2 are calibrated by storing the camera calibration data kal1, kal2 and the processing device correction data norm1, norm2 in the EEPROMs 7-1, 7-2.

FIG. 5 shows a schematic for calculating adapted camera calibration data when exchanging a camera.

FIG. 5 shows a state in which a second camera 5-2b (e.g. a replacement camera), which was calibrated by a second processing device 3b, is connected to a first processing device 3a at the second interface 27-2 of the first processing device 3a. A first camera 5-1a, which was calibrated together with the first processing device 3a, is connected to the first interface 27-1 of the first processing device 3a. Consequently, e.g. in the context of exchanging a defective camera, two cameras 5-2b, 5-1a are connected to the first processing device 3a. The processing device 3a and the cameras 5-1a, 5-2b are otherwise as described above. In accordance with the explanations above, the first camera 5-1 a holds first processing device correction data norm1a of the first processing device 3a and first camera calibration data kal1a of the calibration at the first processing device 3a in its EEPROM 7-1. Analogously thereto, the camera 5-2b holds second processing device correction data norm2b of the second processing device 3b and second camera calibration data kal2b of the calibration at the second processing device 3b in its EEPROM 7-2.

In this configuration, since the second camera 5-2b was calibrated using the characteristics of the second processing device 3b, the second camera calibration data kal2b also include the characteristics of the second processing device 3b, which can be different from the characteristics of the first processing device 3a. As a result, it may be the case that reliably detecting a security feature of a banknote is not able to be carried out. Consequently, adapted first and second camera calibration data kal1', kal2' for the first and second cameras 5-1a, 5-2b or for the first and second signal transmission and signal processing paths 43-1, 43-2 have to be calculated by the first processing device 3a and then used to take account of the characteristics of the first processing device 3a.

For calculating the adapted camera calibration data kal1', kal2', the CPU 21 of the first processing device 3a reads out the first processing device correction data norm1$a$ and the first camera calibration data kal1$a$ from the EEPROM 7-1 of the first camera 5-1$a$, the second processing device correction data norm2$b$ and the second camera calibration data kal2$b$ from the EEPROM 7-2 of the second camera 5-2$b$ and also the first and second processing device correction data norm1$a$, norm2$a$ from the EEPROM 25 of the first processing device 3$a$. The adapted camera calibration data kal1', kal2' are then calculated as follows:

$$kal1' = \frac{norm1a}{norm1a} kal1a \quad (1)$$

$$kal2' = \frac{norm2b}{norm2a} kal2b \quad (2)$$

Consequently, for the case where the second processing device correction data norm2$b$ of the second camera 5-2$b$ are different from the second processing device correction data norm2$a$ of the first processing device 3$a$, this results in a weighting of the second camera calibration data kal2$b$, that is to say that in the adapted second camera calibration data kal2', the characteristics of the first processing device 3$a$ are taken into account and the characteristics of the second processing device 3$b$, at which the second camera 5-2$b$ was calibrated, are extracted by computation. For the adapted first camera calibration data kal1', since the first processing device correction data norm1$a$ of the first camera 5-1$a$ and of the first processing device 3$a$ are identical on account of the calibration of the first camera 5-1$a$ at the first processing device 3$a$, this results in no difference with respect to the first camera calibration data kal1$a$. After the calculation, the CPU 21 stores the adapted camera calibration data kal1', kal2' in the RAM 23 of the first processing device 3$a$ for further use. Since the RAM 23 is a volatile memory, the adapted camera calibration data kal1', kal2', are calculated as soon as they are no longer present in the RAM 23, e.g. upon a system restart.

What is claimed is:

1. A system, comprising:
   a processing device; and
   an exchangeable camera connected thereto for detecting a machine-readable security feature of a valuable document;
   wherein the system is calibrated by means of processing device correction data, which relate to characteristics of the processing device, and camera calibration data, which relate to characteristics of the processing device and of the camera connected thereto, wherein the camera comprises a memory configured to store the processing device correction data and the camera calibration data relating to the system in which the calibration is carried out;
   wherein the processing device comprises a memory configured to store the processing device correction data and the camera calibration data relating to the system in which operation for detecting a machine-readable security feature of the valuable document is carried out; and
   wherein the processing device is configured to calculate the camera calibration data—to be stored in the memory of the processing deviceof the system in which operation for detecting a machine-readable security feature of the valuable document is carried out, by weighting the camera calibration data stored in the memory of the camera with the processing device correction data stored in the memory of the camera and with the processing device correction data stored in the memory of the processing device.

2. The system according to claim 1, wherein the camera comprises an image sensor, preferably a contact image sensor, and an illumination means.

3. The system according to claim 2, wherein the illumination means is an LED which emits radiation in a spectrum coordinated with the spectrum of the image sensor.

4. The system according to claim 3, wherein the camera is embodied as a camera pair comprising a first and a second camera and wherein the first camera is configured to detect reflected light that is emitted by the LED and is reflected by the valuable document, and the second camera is configured to detect transmitted light that is emitted by the LED and passes through the valuable document.

5. The system according to any of the preceding claims, wherein the camera calibration data comprise at least one of the following items of information:
   a white reference value of the camera;
   a camera illumination value;
   a camera colour value;
   a distance value of the camera with respect to the valuable document;
   a transport speed value of the valuable document relative to the camera.

6. The system according to any of the preceding claims, wherein the processing device correction data comprise at least one of the following items of information:
   a camera reference voltage;
   a camera bright level voltage;
   a camera dark level voltage;
   a camera bright level mean value voltage;
   a camera dark level mean value voltage;
   an amplification voltage.

7. The system according to any of the preceding claims, wherein the memory of the camera is a non-volatile memory, preferably an EEPROM.

8. The system according to any of the preceding claims, wherein the memory of the processing device comprises a non-volatile memory, preferably an EEPROM, in which the processing device correction data are
   stored, and a volatile memory, preferably a RAM, in which the camera
   calibration data are stored.

9. The system according to any of the preceding claims, wherein the valuable document is one of the following:
   a banknote;
   a cheque;
   an identity card;
   a passport;
   a ticket;
   a share document.

10. A method for exchanging a camera in a system comprising a processing device and an exchangeable camera connected thereto for detecting a machine-readable security feature of a valuable document, wherein the method comprises:
    exchanging a first camera, which is connected to a first processing device, for a second camera, which is calibrated by means of a second processing device and which has second camera calibration data (kal2$b$) and second processing device correction data in a memory,
    reading out, by means of the first processing device, the second camera calibration data and the second processing device correction data from the memory of the second camera;

calculating, by means of the first processing device, adapted camera calibration data for the system comprising first processing device and second camera by weighting the second camera calibration data (kal2$b$) with the second processing device correction data and with first processing device correction data stored in a memory of the first processing device; and applying, by means of the first processing device, the adapted camera calibration data by means of storage in the memory of the first processing device.

11. The method according to claim 10, wherein the processing device correction data are obtained by:
  connecting a normalization device, which simulates a calibrated camera, to the processing device;
  outputting, by means of the normalization device, a simulated camera signal; and
  determining, by means of the processing device, the processing device correction data on the basis of the simulated camera signal.

12. The method according to claim 11, wherein the processing device is normalized using the normalization device by storing the determined processing device correction data in the memory of the processing device.

13. The method according to claim 12, wherein the camera calibration data are obtained by:
  connecting a camera to be calibrated to the normalized processing device,
  detecting, by means of the camera, a calibration standard and outputting a corresponding camera signal to the processing device, and
  determining the camera calibration data on the basis of the camera signal that is output to the processing device in response to the calibration standard.

14. The method according to claim 13, wherein the camera is calibrated using the normalized processing device by storing the determined camera calibration data together with processing device correction data of the processing device in the memory of the camera.

* * * * *